United States Patent

Iijima et al.

[11] Patent Number: 4,625,032
[45] Date of Patent: Nov. 25, 1986

[54] TETRAHYDRO-β-CARBOLINE DERIVATIVES

[75] Inventors: Ikuo Iijima, Urawa; Yutaka Saiga, Ageo; Toshikazu Miyagishima, Wako; Yuzo Matsuoka, Tondabayashi; Mamoru Matsumoto, Nara, all of Japan

[73] Assignee: Tanabe Seiyaku Co., Ltd., Osaka, Japan

[21] Appl. No.: 741,133

[22] Filed: Jun. 4, 1985

[30] Foreign Application Priority Data

Jun. 6, 1984 [GB] United Kingdom ............... 8414409
Jun. 30, 1984 [GB] United Kingdom ............... 8416719
Sep. 18, 1984 [GB] United Kingdom ............... 8423551

[51] Int. Cl.$^4$ ............................................. C07D 31/435
[52] U.S. Cl. ................................................ 546/81
[58] Field of Search ........................... 546/81; 514/292

[56] References Cited

U.S. PATENT DOCUMENTS 2,187,719  6/1938  Williams .......................... 546/81
4,336,260  6/1982  Payne et al. ...................... 546/85
4,522,947  6/1985  Musser et al. ..................... 546/81

FOREIGN PATENT DOCUMENTS 20923   1/1958  Fed. Rep. of Germany ........ 546/81
894620  4/1964  France ............................ 546/85

Primary Examiner—Henry R. Jiles
Assistant Examiner—J. Richter
Attorney, Agent, or Firm—Birch, Stewart, Kolasch & Birch

[57] ABSTRACT

Tetrahydro-β-carboline derivative of the formula:

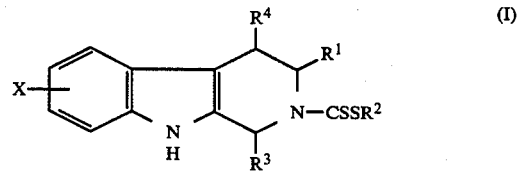

(I)

wherein $R^2$ is lower alkyl, and either (A)
  $R^1$ is hydroxymethyl or carboxy,
  $R^3$ and $R^4$ are both hydrogen, and
  X is halogen, lower alkyl, lower alkoxy, hydroxy or benzyloxy; or (B)
  $R^1$ is hydrogen, carboxy-lower alkyl or a group of the formula: —CH$_2$OY,
  Y is lower alkyl, lower alkanoyl or an oxygen-containing monocyclic heterocyclic group,
  $R^3$ is hydrogen, hydroxy-lower alkyl or carboxy,
  $R^4$ is hydrogen or hydroxy-lower alkyl, and
  X is hydrogen, or a salt thereof, which has excellent activities for alleviating, curing and preventing hepatic damages and is useful as a therapeutic or prophylactic agent for hepatic diseases.

6 Claims, No Drawings

TETRAHYDRO-β-CARBOLINE DERIVATIVES

This invention relates to a novel tetrahydro-β-carboline derivative of the formula:

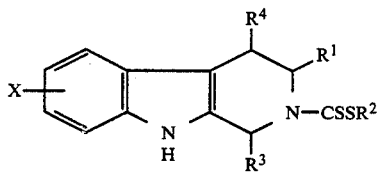

wherein $R^2$ is a lower alkyl, and either (A)
$R^1$ is hydroxymethyl or carboxy,
$R^3$ and $R^4$ are both hydrogen, and
X is halogen, lower alkyl, lower alkoxy, hydroxy or benzyloxy; or (B)
$R^1$ is hydrogen, carboxy-lower alkyl or a group of the formula: —CH$_2$OY, wherein
Y is lower alkyl, lower alkanoyl or an oxygen-containing monocyclic heterocyclic group,
$R^3$ is hydrogen, hydroxy-lower alkyl or carboxy,
$R^4$ is hydrogen or hydroxy-lower alkyl, and
X is hydrogen;
or a salt thereof, and processes for preparation thereof.

The liver is an organ having various functions such as detoxification, carbohydrate metabolism, lipid metabolism, protein metabolism, production and secretion of bile, production of blood coagulation factors, control of hormones, regeneration of liver cells, storage of living body-constituting elements (e.g. fats, glycogen, proteins, vitamins) and the like. These functions are acutely or chronically disordered by various causes such as virus, drugs, poisons, alcohols, insufficient nutrition, vascular dysfunction of the liver, obstruction of the bile duct, or the like. These liver function disorders appear clinically in the form of viral hepatitis, drug-induced hepatopathy, alcoholic hepatitis, congestive hepatitis, hepatic disease caused by bile-congestion, fatty liver, jaundice, hepatocirrhosis and the like.

The tetrahydro-β-carboline derivatives of the formula (I) are useful as therapeutic or prophylactic agents for hepatic diseases, because they show excellent activities for alleviating or curing hepatic damages and also for protecting the liver from hepatic damages.

Representative examples of the compound of the present invention include those of the formula (I) in which $R^2$ is lower alkyl (e.g. methyl, ethyl, propyl or butyl), and either (A) $R^1$ is hydroxymethyl or carboxy, $R^3$ and $R^4$ are both hydrogen, and X is halogen (e.g. fluorine, chlorine, bromine or iodine), lower alkyl (e.g. methyl, ethyl, propyl or butyl), lower alkoxy (e.g. methoxy, ethoxy, propoxy or butoxy), hydroxy or benzyloxy; or (B) $R^1$ is hydrogen, carboxy-lower alkyl (e.g. carboxymethyl, carboxyethyl, carboxypropyl or carboxybutyl) or a group of the formula: —CH$_2$OY, Y is lower alkyl (e.g. methyl, ethyl, propyl or butyl), lower alkanoyl (e.g. acetyl, propionyl or butyryl) or an oxygen-containing monocyclic heterocyclic group (e.g. tetrahydropyranyl, dihydropyranyl or tetrahydrofuryl), $R^3$ is hydrogen, hydroxy-lower alkyl (e.g. hydroxymethyl, hydroxyethyl, hydroxypropyl or hydroxybutyl) or carboxy, $R^4$ is hydrogen or hydroxy-lower alkyl (e.g. hydroxymethyl, hydroxyethyl, hydroxypropyl or hydroxybutyl), and X is hydrogen.

Preferred compounds are those of the formula (I) in which $R^2$ is methyl or ethyl, and either (A) $R^1$ is hydroxymethyl or carboxy, $R^3$ and $R^4$ are both hydrogen, and X is fluorine, chlorine, bromine, methyl, methoxy, hydroxy or benzyloxy; or (B) $R^1$ is hydrogen, carboxymethyl or a group of the formula: —CH$_2$OY, Y is methyl, acetyl or tetrahydropyranyl, $R^3$ is hydrogen, hydroxymethyl, hydroxypropyl or carboxy, $R^4$ is hydrogen or hydroxymethyl and X is hydrogen.

A salt of the compound (I) in which $R^1$ is carboxy or carboxy-lower alkyl, or $R^3$ is carboxy, is also included within the scope of the present invention. Suitable examples of the salt of the compound (I) include metallic salts (e.g. sodium, potassium or calcium salt), an ammonium salt or organic amine salts (e.g. trimethylamine, triethylamine or 2-aminoethanol salt).

The compound (I) of the present invention can exist in the form of eight isomers when none of $R^1$, $R^3$, and $R^4$ is hydrogen; in the form of four isomers when either one of $R^1$, $R^3$ and $R^4$ is hydrogen; or in the form of two isomers when two of $R^1$, $R^3$ and $R^4$ are hydrogen.

In any case, all of these isomers and/or a mixture thereof are included within the scope of the invention.

According to the present invention, the compound (I) may be prepared by reacting a compound of the formula:

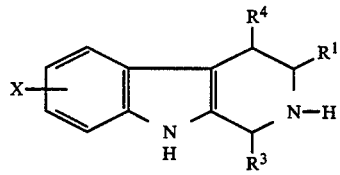

wherein $R^1$, $R^3$, $R^4$ and X are the same as defined above, or a salt thereof, with carbon disulfide and a compound of the formula:

$$R^2-X^1 \qquad (III)$$

wherein $X^1$ is halogen, and $R^2$ is the same as defined above. Examples of the salt of the compound (II) include oxalate, hydrochloride and hydrobromide. The compound (III) in which $X^1$ is chlorine, bromine or iodine is preferably used in the reaction. The reaction is preferably carried out in the presence of a base in a solvent. Examples of the base include inorganic bases such as alkali metal hydroxides (e.g. sodium hydroxide or potassium hydroxide), alkali metal carbonate (e.g. sodium carbonate or potassium carbonate) and organic bases (e.g. triethylamine, N-methylmorpholin or N,N-dicyclohexylamine). Examples of the solvent include alkanol (e.g. methanol or ethanol), dimethylsulfoxide, N,N-dimethylformamide, dioxane, tetrahydrofuran, water and a mixture thereof. It is preferred to carry out the reaction at a temperature of 0° to 50° C., especially 10° to 30° C.

Among the compounds of the present invention, a compound of the formula:

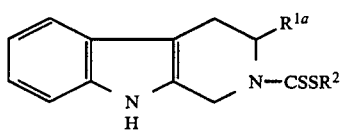     (I-a)

wherein $R^{1a}$ is a group of the formula: —CH$_2$OY$^a$, Y$^a$ is lower alkyl, and R$^2$ is the same as defined above, may be prepared by reacting a compound of the formula:

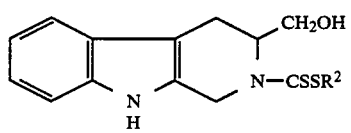     (IV)

wherein R$^2$ is the same as defined above, with diazo-lower alkane. Examples of the diazo-lower alkane include diazomethane, diazoethane, diazopropane and diazobutane. The reaction may be carried out in the presence of silica gel in a solvent. Ether, dioxane, tetrahydrofuran and the like are suitable as the solvent. It is preferred to carry out the reaction at a temperature of 0° to 30° C.

A compound of the formula:

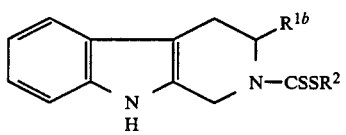     (I-b)

wherein $R^{1b}$ is a group of the formula: —CH$_2$OY$^b$, Y$^b$ is lower alkanoyl, and R$^2$ is the same as defined above, may be prepared by reacting a compound (IV) with lower alkanoic acid or a reactive derivative thereof. Examples of the reactive derivative of lower alkanoic acid include acid anhydride (e.g. acetic anhydride, propionic anhydride or butyric anhydride) and acid halide (e.g. acetyl chloride, acetyl bromide, propionyl chloride or butyryl chloride). The reaction of the compound (IV) with the acid anhydride or the acid halide is preferably carried out in the presence of an acid acceptor in a solvent. The acid acceptor includes, for example, pyridine, triethylamine, N-methylmorpholin and the like. Pyridine, N,N-dimethylformamide, N,N-dimethylacetamide, chloroform, tetrahydrofuran and the like are suitable as the solvent. When pyridine is used as the solvent, it may serve as the acid acceptor. It is preferred to carry out the reaction at a temperature of 0° to 50° C. when the acid anhydride is used as the reactive derivative. On the other hand, when the acid halide is used as the reactive derivative, it is preferred to carry out the reaction at a temperature of 0° to 30° C.

Alternatively, the reaction of the compound (IV) with the lower alkanoic acid is preferably carried out in the presence of a condensing agent in a solvent. The condensing agent includes, for example, N,N'-dicyclohexylcarbodiimide and the like. Tetrahydrofuran, ether, dimethylformamide, dioxane and the like are suitable as the solvent. It is preferred to carry out the reaction at a temperature of 0° to 80° C.

Further, a compound of the formula:

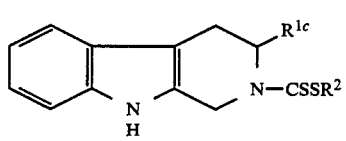     (I-c)

wherein $R^{1c}$ is a group of the formula: —CH$_2$OY$^c$, Y$^c$ is an oxygen-containing monocyclic heterocyclic group, and R$^2$ is the same as defined above, may be prepared by reacting a compound (IV) with an unsaturated oxygen-containing monocyclic heterocyclic compound. Examples of the unsaturated oxygen-containing monocyclic heterocyclic compound include dihydropyran, pyran and dihydrofuran. The reaction may be carried out in the presence of an acid catalyst in a solvent. Examples of the acid catalyst include toluenesulfonic acid, hydrochloric acid, sulfuric acid and the like. Acetonitrile, tetrahydrofuran, dioxane, ether, chloroform, methylene chloride, benzene and the like are suitable as the solvent. It is preferred to carry out the reaction at a temperature of 0° to 50° C.

The compound of the formula (I) wherein R$^1$ is carboxy or carboxymethyl or R$^3$ is carboxy may be, if required, converted into a salt thereof by treating it with an inorganic or organic base such as alkali metal hydroxide (e.g. sodium hydroxide or potassium hydroxide), alkaline earth metal hydroxide (e.g. calcium hydroxide), ammonia, trialkyl amine (e.g. trimethylamine or triethylamine) or 2-aminoethanol.

The starting compound (II) may be prepared according to the processes as shown in the reaction schemes:

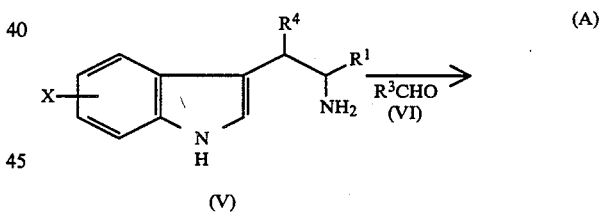     (A)

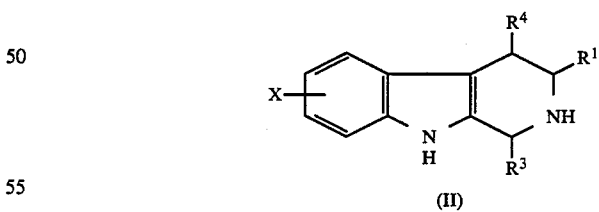     (II)

wherein R$^1$, R$^3$, R$^4$ and X are the same as defined above.

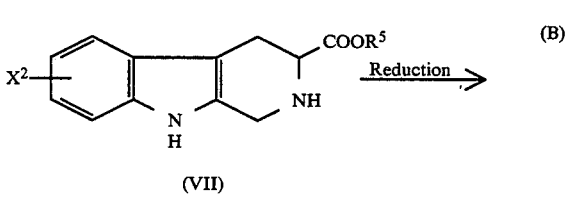     (B)

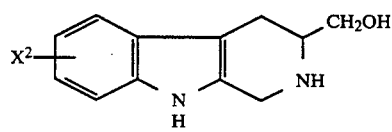
(II-a)
wherein $X^2$ is halogen, lower alkyl, lower alkoxy, hydroxy or benzyloxy, and $R^5$ is an ester residue.
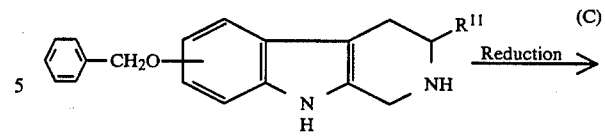
(VIII)                                           (C)
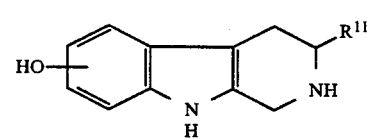
(II-b)
wherein $R^{11}$ is hydroxymethyl or carboxy.
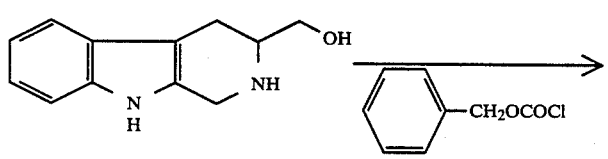
(IX)                                             (D)
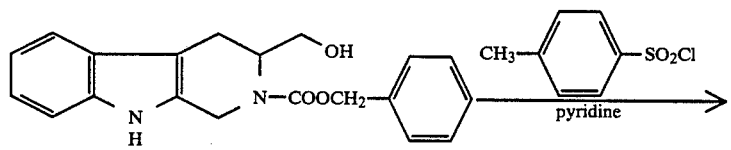
(X)
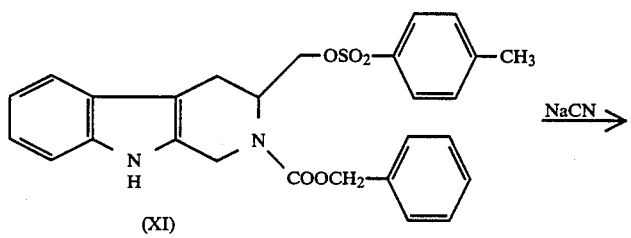
(XI)
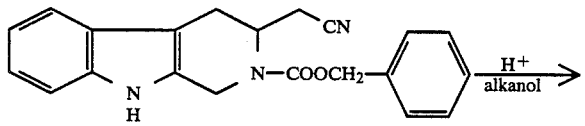
(XII)
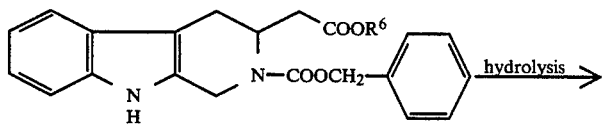
(XIII)
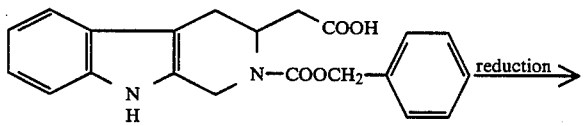
(XIV)

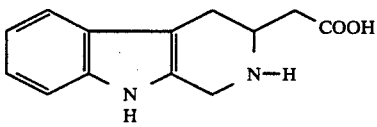

(II-c)

wherein R⁶ is an ester residue.

On the other hand, the starting compound (IV) may be prepared according to the process as shown in the reaction scheme:

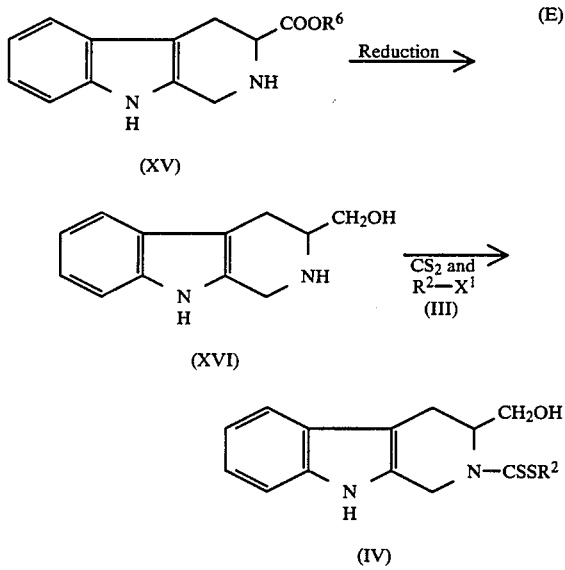

wherein R⁶ is an ester residue, and R² and X¹ is the same as defined above.

According to the method (A), the compound (II) may be prepared by reacting the compound (V) or a salt thereof (e.g. hydrochloride, hydrobromide or oxalate) with the compound (VI) at 20° to 100° C. in a solvent (e.g. methanol, ethanol, water or a mixture thereof).

According to the method (B), the compound (II-a) may be prepared by reducing the compound (VII) or a salt thereof (e.g. oxalate, hydrochloride or hydrobromide) with a reducing agent (e.g. lithium aluminum hydride or sodium borohydride) at 0° to 100° C. in a solvent (e.g. tetrahydrofuran, dimethoxyethane, dioxane, methanol, ethanol or water).

According to the method (C), the compound (II-b) may be prepared by reducing the compound (VIII) in the presence of a catalyst (e.g. palladium-charcoal, palladium-black, palladium-barium sulfate or platinum oxide) at 20° to 80° C. in a solvent (e.g. methanol, ethanol, ethyl acetate, tetrahydrofuran, aqueous ethanol, aqueous methanol or acetic acid) under atmospheric or increased pressure.

According to the method (D), the compound (II-c) may be prepared by reacting the compound (IX) with benzyloxycarbonyl chloride at 5° to 10° C. in the presence of an acid acceptor (e.g. triethylamine) in a solvent (e.g. methanol), reacting the compound (X) with p-toluenesulfonyl chloride at 5° C. in a solvent (e.g. pyridine), reacting the compound (XI) with sodium cyanide at 5° to 30° C. in a solvent (e.g. dimethylformamide), treating the compound (XII) with hydrogen chloride in a solvent (e.g. methanol) at 5° C., hydrolyzing the compound (XIII) with a base (e.g. sodium hydroxide) in a solvent (e.g. aqueous tetrahydrofuran), and then catalytically reducing the compound (XIV) in the presence of a catalyst (e.g. palladium-charcoal) in a solvent (e.g. aqueous ethanol).

Further, according to the method (E), the compound (IV) may be prepared by reducing the compound (XV) (this compound may be prepared in a known manner per se such as those described in J. Med. Chem., 16, 418 (1973); Yakugaku Zasshi, 98, 1635 (1978); J. Org. Chem., 44, 535 (1979); J. Am. Chem. Soc., 102, 6976 (1980); J. Org. Chem., 46, 164 (1981) and J. Med. Chem., 25, 1081 (1982)) or a salt thereof (e.g. oxalate, hydrochloride or hydrobromide) with a reducing agent (e.g. lithium aluminum hydride or sodium borohydride) to give the compound (XVI), and then reacting the compound (XVI) with carbon disulfide and the compound (III) in the same manner as the reaction of the compound (II) with carbon disulfide and the compound (III).

There are a known variety of causal factors inducing toxic liver damage, hepatitis and fatty liver. The predominant changes observed in these diseases are necrosis of liver cells, mesenchymal reaction and accumulation of lipid. The feature of necrosis depends on the causal factor and it can be classified into centrilobular necrosis, periportal necrosis and discrete lobular necrosis. Experimentally, the centrilobular necrosis is induced by carbon tetrachloride, and the degree of liver damage is determined by the measurement of liver weight and observation of the liver color with the naked eye. The periportal necrosis and the discrete lobular necrosis associated with mesenchymal reaction are induced by allyl alcohol and D-galactosamine, respectively, and the degree of liver damage is determined by the measurement of activities of glutamic-pyruvic-transaminase (GPT) and glutamic-oxaloacetic-transaminase (GOT) in the blood plasma.

The compounds (I) or pharmaceutically acceptable salts thereof of the present invention have excellent activities for curing, preventing and alleviating various liver diseases, particularly liver diseases associated with centrilobular necrosis; liver diseases associated with periportal necrosis; liver diseases associated with discrete lobular necrosis and mesenchymal reaction; fatty liver; drug-induced hepatopathy; and congestive hepatitis. Accordingly, the compounds (I) or pharmaceutically acceptable salts thereof of the present invention are useful as a therapeutic or prophylactic agent of hepatic diseases in animals including human, and are used, for example, for treating or preventing various diseases such as viral hepatitis, drug-induced hepatopathy, alcoholic hepatitis, fatty liver, jaundice, and also, the final symptom, i.e., hepatocirrhosis. Moreover, the compounds (I) or pharmaceutically acceptable salts thereof of the present invention also show stimulation of the liver function. Further, the compounds (I) or pharmaceutically acceptable salts thereof of the present invention have an activity of inhibiting undesirable production of lipid peroxides. Lipid peroxide levels in tissues of mammalian species are known to increase with age and to cause cell death and/or damage with a consequent change of cell permeability. In addition, lipid peroxides have been suggested to be a primary etiologic factor in the genesis of stroke (cf. Stroke, Vol. 10, No. 3, pages 323–326 (1979)). Thus, the compounds (I) or pharmaceutically acceptable salts thereof may be used to improve the lipid peroxide levels in the tissues of the aged subjects.

When the compounds (I) or pharmaceutically acceptable salts thereof of the present invention are used as a medicine, they can be administered in oral route or parenteral route (e.g. intravenous, intramuscular or subcutaneous route). The dose of the compounds (I) or pharmaceutically acceptable salts thereof may vary according to ages, weights and states of patients, severity of diseases or the like, but is usually in the range of about 0.01 to 250 mg/kg/day, preferably 0.1 to 50 mg/kg/day. Particularly preferred dose of the compounds (I) or pharmaceutically acceptable salts thereof of the present invention in the case of oral administration is in the range of about 0.1 to 250 mg/kg/day, especially 0.5 to 50 mg/kg/day.

The compounds (I) or pharmaceutically acceptable salts thereof can be used in the form of conventional pharmaceutical preparations in admixture with conventional pharmaceutical carriers or diluents which are usually used for oral or parenteral preparations. The carriers include, for example, gelatine, lactose, glucose, sodium chloride, starch, magnesium stearate, talc, vegetable oils and the like. The pharmaceutical preparations may be solid preparations such as tablets, sugar-coating tablets, pills or capsules, or liquid preparations such as solutions, suspensions or emulsions. These preparations may be sterilized. Moreover, various auxiliaries, stabilizers, wetting agents, emulsifiers or any other additives may optionally be added to the preparations.

The present invention is illustrated by the following Experiments, Examples and Preparations, but it should not be construed to be limited thereto.

Throughout the specification and claims, the term "lower alkyl", "lower alkoxy" and "lower alkanoyl" should be interpreted as referring to alkyl of one to 4 carbon atoms, alkoxy of one to 4 carbon atoms and alkanoyl of 2 to 4 carbon atoms, respectively.

EXPERIMENT 1

(Protection against acute carbon tetrachloride-induced liver damage)

Method

A test compound was suspended in 0.5% carboxylmethyl cellulose solution, and the suspension (test compound: 100 mg/10 ml/kg) was orally administered to ddY male mice (age: 5–6 weeks old, weight: 25–30 g, one group: 3 mice), and the animals were fasted. After 3 hours, a solution of carbon tetrachloride in olive oil was orally administered in a dose of 50 μl/5 ml olive oil/kg. After 3 hours, the test compound was again orally administered in the same dose as above. Weight of the animals was measured 24 hours after $CCl_4$-administration, and then the animals were killed. Immediately, the liver was taken out, weighed and macroscopically observed. As the normal control, 0.5% carboxymethyl cellulose solution and olive oil were orally administered to the animals instead of the suspension of test compound and the $CCl_4$-solution. Besides, the $CCl_4$-control group was given the $CCl_4$-solution and 0.5% carboxymethyl cellulose solution.

The therapeutic effect of the test componds on liver damages was evaluated based on the suppressive % of the increase of relative liver weight calculated by the following equation and also based on the macroscopic observation of the liver. The term "relative liver weight" means weight (g) of the liver/100 g body weight.

Suppressive % of the increase of relative liver weight =

$$\left(1 - \frac{\begin{array}{l}\text{Mean of relative} \\ \text{liver weight in} \\ \text{test compound} \\ \text{group}\end{array} - \begin{array}{l}\text{Mean of relative} \\ \text{liver weight in} \\ \text{normal control} \\ \text{group}\end{array}}{\begin{array}{l}\text{Mean of relative} \\ \text{liver weight in} \\ CCl_4\text{-control} \\ \text{group}\end{array} - \begin{array}{l}\text{Mean of relative} \\ \text{liver weight in} \\ \text{normal control} \\ \text{group}\end{array}}\right) \times 100$$

TABLE 1

| Macroscopic observation of the liver | (Criteria) Suppressive % of the increase of relative liver weight | | |
|---|---|---|---|
| | $\geq 20\%$ | $\geq -20\%$ to $<20\%$ | $< -20\%$ |
| Almost the same as normal control group | AA | C | D |
| Showed a sign of amelioration from $CCl_4$ - control group | A | C | D |
| Showed the same color or appearance as in $CCl_4$ - control group | B | D | D |

Remarks:
AA means "significantly effective",
A, B and C mean "effective", and
D means "not effective".

Results

The following compounds are "significantly effective" against acute carbon tetrachloride-induced liver damage.

TABLE 2

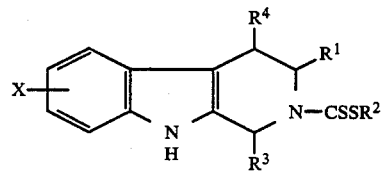

| $R^1$ | $R^2$ | $R^3$ | $R^4$ | X | configuration |
|---|---|---|---|---|---|
| $CH_2OH$ | $CH_3$ | H | H | 6-F | 3S |
| $CH_2OH$ | $CH_3$ | H | H | 6-Cl | 3S |
| $CH_2OH$ | $CH_3$ | H | H | 6-Br | 3S |
| $CH_2OH$ | $CH_3$ | H | H | 6-$CH_3$ | 3S |
| $CH_2OH$ | $CH_3$ | H | H | 8-$CH_3$ | 3S |
| $CH_2OH$ | $CH_3$ | H | H | 6-OH | 3S |
| COOH | $CH_3$ | H | H | 6-F | 3S |
| COOH | $CH_3$ | H | H | 6-$CH_3$ | 3S |
| COOH | $CH_3$ | H | H | 6-$OCH_3$ | 3S |
| COOH | $CH_3$ | H | H | 8-$CH_3$ | 3S |
| $CH_2COOH$ | $CH_3$ | H | H | H | 3S |
| H | $CH_3$ | COOH | H | H | 1RS |
| H | $CH_3$ | $CH_2OH$ | H | H | 1RS |
| H | $C_2H_5$ | $CH_2OH$ | H | H | 1RS |

TABLE 2-continued

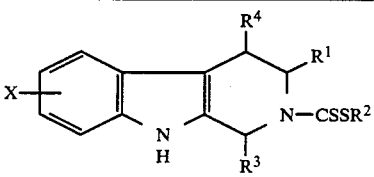

| $R^1$ | $R^2$ | $R^3$ | $R^4$ | X | configuration |
|---|---|---|---|---|---|
| H | $CH_3$ | $C_3H_6OH$ | H | H | 1RS |
| H | $CH_3$ | H | $CH_2OH$ | H | 4RS |
| $CH_2OCOCH_3$ | $CH_3$ | H | H | H | 3S |
| $CH_2OCH_3$ | $CH_3$ | H | H | H | 3S |

EXPERIMENT 2

(Preventive effect on lipid peroxide formation)

Method 0.1 ml of a dimethylsulfoxide solution containing $3 \times 10^{-3}$M of a test compound was added to a mixture of 2.4 ml of 0.067M potassium phosphate buffer solution (pH 7.4) and 0.5 ml of 10% rat brain-homogenate (final concentration of the test compound: $10^{-4}$M). After a one-hour incubation of the mixture at 37° C., one ml of 20% trichloroacetic acid was added thereto, and lipid peroxide formations were determined by the thiobarbituric acid colorimetric method (J. Robak et al., Biochem. Pharmacol., Vol. 25, page 2233 (1976)). Percentage inhibition of lipid peroxide formation of the test compound was calculated according to the following equation:

$$\text{Inhibitory (\%) of lipid peroxide formation} = \left(1 - \frac{\Delta OD \text{ of test tube*}}{\Delta OD \text{ of control tube**}}\right) \times 100$$

Note:
*tube containing the test compound
**tube containing an equal volume of dimethylsulfoxide instead of the test compound solution
$\Delta OD$ was calculated as [(optical density measured at 532 nm) − (optical density measured at 600 nm)]

Results

The preventive effects on the lipid peroxide formation of the test compounds are shown in Table 2.

TABLE 3

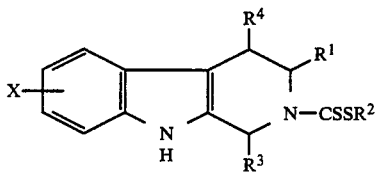

| $R^1$ | $R^2$ | $R^3$ | $R^4$ | X | configuration | Inhibitory % |
|---|---|---|---|---|---|---|
| $CH_2OH$ | $CH_3$ | H | H | 6-$CH_3$ | 3S | 92.8 |
| $CH_2OH$ | $CH_3$ | H | H | 8-$CH_3$ | 3S | 94.2 |
| $CH_2OH$ | $CH_3$ | H | H | 6-OCH$_2$–C$_6$H$_5$ | 3S | 98.3 |
| $CH_2OH$ | $CH_3$ | H | H | 6-OH | 3S | 92.8 |
| H | $CH_3$ | $CH_2OH$ | H | H | 1RS | 94.2 |
| H | $C_2H_5$ | $CH_2OH$ | H | H | 1RS | 84.7 |
| H | $CH_3$ | $C_3H_6OH$ | H | H | 1RS | 89.9 |
| H | $CH_3$ | H | $CH_2OH$ | H | 4RS | 82.1 |
| $CH_2OCH_3$ | $CH_3$ | H | H | H | 3S | 86.5 |
| $CH_2O$-tetrahydropyranyl | $CH_3$ | H | H | H | 3S | 94.5 |
| $CH_2O$-tetrahydropyranyl | $CH_3$ | H | H | H | 3S | |

EXAMPLE 1

0.22 g of (3S)-3-hydroxymethyl-6-fluoro-1,2,3,4-tetrahydro-β-carboline is dissolved in a mixture of 2 ml of dimethylsulfoxide and 1 ml of water. 0.17 ml of triethylamine and 0.07 ml of carbon disulfide are added thereto. The mixture is stirred at room temperature for 30 minutes. 0.075 ml of methyl iodide is added thereto, and the mixture is further stirred at room temperature for 6 hours. The reaction mixture is poured into ice-water and the aqueous solution is extracted with ethyl acetate. The extract is washed with water, dried and then evaporated to remove solvent, whereby 295 mg of methyl (3S)-3-hydroxymethyl-6-fluoro-1,2,3,4-tetrahydro-β-carboline-2-carbodithioate are obtained as pale yellow powder. Yield: 95%.

$[\alpha]_D^{20}$ +132.0° (C=0.5, methanol).

NMR (CDCl$_3$, δ): 2.68 (s, 3H, —CSSCH$_3$).

Mass (m/e): 310 (M+), 262 (M+—CH$_3\overline{SH}$).

EXAMPLES 2 TO 7

In the same manner as described in Example 1, the following compounds are obtained.

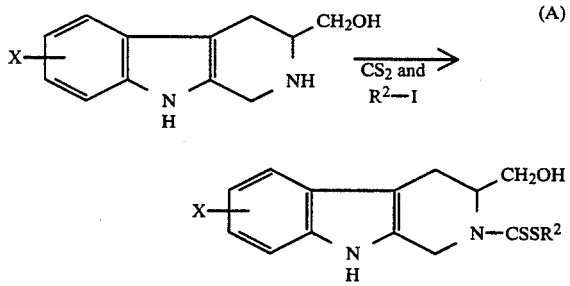

EXAMPLE 8

65 mg of (3S)-6-fluoro-1,2,3,4-tetrahydro-β-carboline-3-carboxylic acid are dissolved in a mixture of one ml of dimethylsulfoxide and 0.5 ml of water. 0.02 ml of carbon disulfide and 0.093 ml of triethylamine are added to the mixture, and the mixture is stirred at room temperature for 20 minutes. 0.021 ml of methyl iodide is added to the mixture, and the mixture is stirred at room temperature for 16 hours. Water is added to the mixture, and the aqueous solution is acidified with 10% HCl and extracted with ethyl acetate. The extract is washed with water, dried and then evaporated to remove the solvent. The residue is purified by silica gel thin layer chromatography (Solvent; chloroform:methanol:acetic acid=93:6:1). 37 mg of (3S)-6-fluoro-2-(methylthio)thiocarbonyl-1,2,3,4-tetrahydro-β-carboline-3-carboxylic acid are obtained as pale yellow powder.

TABLE 4

| Example Nos. | Compounds (A)* R² | X | Yield (%) | Physical properties |
|---|---|---|---|---|
| 2 | CH₃ | 6-Cl | 86 | M.p. 180 to 184° C., pale yellow prisms [α]$_D^{20}$ + 98° (C = 1.0, methanol) NMR (CDCl₃ + DMSO—d₆, δ): 2.70 (s, 3H, —CSSC$\underline{H}_3$) Mass (m/e): 328, 326 (M⁺), 280, 278 (M⁺—CH₃SH) |
| 3 | CH₃ | 6-Br | 37.7 | pale yellow powder [α]$_D^{20}$ + 72.0° (C = 0.2, methanol) NMR (CDCl₃, δ): 2.71 (s, 3H, —CSSC$\underline{H}_3$) Mass (m/e): 372, 370 (M⁺), 324, 322 (M⁺—CH₃SH) |
| 4 | CH₃ | 6-CH₃ | 78 | M.p. 170 to 172° C., colorless prisms [α]$_D^{20}$ + 108.0° (c = 1.0, methanol) NMR (CDCl₃, δ): 2.43 (s, 3H, C$\underline{H}_3$—⟨⟩—), 2.70 (s, 3H, —CssC$\underline{H}_3$), Mass (m/e): 306 (M⁺), 258 (M⁺—CH₃SH) |
| 5 | CH₃ | 8-CH₃ | 83 | white powder [α]$_D^{20}$ + 199.2° (C = 1.0, methanol) NMR (CDCl₃, δ): 2.43 (s, 3H, ⟨⟩—C$\underline{H}_3$) 2.66 (s, 3H, —CSSC$\underline{H}_3$) Mass (m/e): 306 (M⁺), 258 (M⁺—CH₃SH) |
| 6 | CH₃ | 6-O—CH₂—⟨⟩ | 59 | pale yellow powder [α]$_D^{20}$ + 57° (C = 1.0, methanol) NMR (CDCl₃, δ): 5.08 (s, 2H, —O—C$\underline{H}_2$—⟨⟩) 2.69 (s, 3H, —CSSC$\underline{H}_3$) Mass (m/e): 398 (M⁺), 350 (M⁺—CH₃SH) |
| 7 | CH₃ | 6-OH | 61 | pale yellow powder [α]$_D^{20}$ + 116.0° (C = 0.2, methanol) NMR (CDCl₃ + DMSO—d₆; δ): 2.71 (s, 3H, —CSSC$\underline{H}_3$) Mass (m/e): 308 (M⁺), 260 (M⁺—CH₃SH) |

*The compounds listed in the Table are all (3S)—isomers.

NMR (CDCl₃, δ): 2.68 (S, 3H, —CSSCH₃).
Mass (m/e): 324 (M+), 276 (M+—CH₃S̄H).
[α]$_D^{20}$+205.0° (C=0.2, methanol).

EXAMPLES 9 TO 13

In the same manner as described in Example 8, the following compounds are obtained.

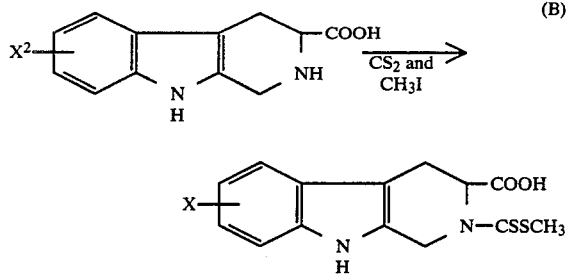

TABLE 5

| | Compound (B) | |
|---|---|---|
| Example Nos. | X | Configuration | Physical properties and others |
| 9 | 6-Cl | 3R | White powder<br>NMR (CDCl₃ + DMSO-d₆, δ):<br>2.79 (s, 3H, —CSSC$\underline{H}_3$)<br>Mass (m/e): 342, 340 (M+), 294, 292 (M+—CH₃SH)<br>[α]$_D^{20}$ −210.8°(C = 0.5, methanol) |
| 10 | 6-CH₃ | 3S | Colorless needles<br>M.p. 200–201° C.<br>NMR (CDCl₃, δ):<br>2.24 (s, 3H, C$\underline{H}_3$— 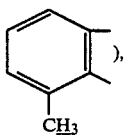 )<br>2.72 (s, 3H, —CSSC$\underline{H}_3$)<br>Mass (m/e): 320 (M+), 272 (M+—CH₃SH)<br>[α]$_D^{20}$ + 240.8° (C = 0.8, methanol)<br>Yield: 66% |
| 11 | 6-OH | 3RS | Pale yellow powder<br>NMR (CDCl₃ + DMSO-d₆, δ):<br>2.71 (s, 3H, —CSSC$\underline{H}_3$) |
| 12 | 6-OCH₃ | 3S | White powder<br>NMR (CDCl₃, δ): 2.66 (s, 3H, —CSSC$\underline{H}_3$), 3.80 (s, 3H, CH₃O—⌬)<br>Mass (m/e): 336 (M+):<br>288 (M+—CH₃SH)<br>[α]$_D^{20}$ + 228.6° (C = 1.0, methanol)<br>Yield: 52% |
| 13 | 6-OCH₂—⌬ | 3S | Pale yellow powder<br>NMR (CDCl₃, δ): 2.64 (s, 3H, —CSSC$\underline{H}_3$),<br>5.00 (s, 2H, —OC$\underline{H}_2$—⌬)<br>Mass (m/e): 364 (M+—CH₃SH)<br>[α]$_D^{20}$ + 159.0° (C = 1.0, ethanol) |

EXAMPLE 14

610 mg of methyl (3S)-8-methyl-1,2,3,4-tetrahydro-β-carboline-3-carboxylate are dissolved in 20 ml of methanol, and 2 ml of a 10% aqueous sodium hydroxide solution are added thereto. The mixture is stirred at room temperature for 3 hours. One ml of a 10% aqueous sodium hydroxide solution and 228 mg of carbon disulfide are added to the mixture, and the mixture is stirred at room temperature for 30 minutes. Then, 355 mg of methyl iodide are adde to the mixture, and the mixture is stirred at the same temperature for 2.5 hours. After the reaction, the mixture is evaporated to remove the solvent. The residue is dissolved in water, and the aqueous solution is extracted with ethyl acetate. The aqueous layer is acidified with 10% HCl, and then extracted with ethyl acetate. The extract is washed with water, dried and then evaporated to remove the solvent. A mixture of ether and n-hexane is added to the residue, and the precipitates are collected. 200 mg of (3S)-8-methyl-2-(methylthio)thiocarbonyl-1,2,3,4-tetrahydro-β-carboline-3-carboxylic acid are obtained as white powder.

NMR (CDCl₃, δ): 2.39 (s, 3H, ⌬-CH₃), 2.68 (s, 3H, —CSSCH₃)
Mass (m/e): 320 (M̄+), 272 (M+—CH₃SH).

EXAMPLE 15

235 mg of (3S)-1,2,3,4-tetrahydro-β-carboline-3-acetic acid hydrochloride are dissolved in 2 ml of dimethylsulfoxide. 0.42 ml of triethylamine and 0.07 ml of carbon disulfide are added to the mixture, and the mixture is stirred at room temperature for 30 minutes. Then, 0.07 ml of methyl iodide are added dropwise to the mixture. The mixture is further stirred at the same temperature for 2 hours. The reaction mixture is evaporated to remove the solvent, and the residue is dissolved in water. The aqueous solution is acidified with 5% HCl, and extracted with ethyl acetate. The extract is washed with water, dried and then evaporated to remove the solvent. Aqueous ethanol is added to the residue, and the precipitates are collected. 102 mg of (3S)-2-(methylthio)thiocarbonyl-1,2,3,4-tetrahydro-β-carboline-3-acetic acid are obtained as white powder.

NMR (DMSO-d₆, δ): 2.62 (s, 3H), CSSCH₃).
Mass (m/e): 320 (M+), 272 (M+—CH₃S̄H).
[α]$_D^{20}$+184.0° (c=0.1, methanol).

EXAMPLE 16

In the same manner as described in Example 15, the following compound is obtained.

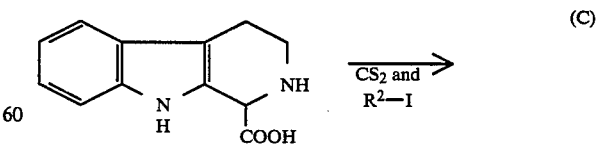

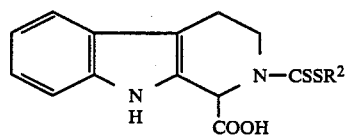

TABLE 6

| Example Nos. | Compound (C) R² | Configuration | Physical properties |
|---|---|---|---|
| 16 | CH₃ | 1RS | Colorless needles M.p. 150–151° C. (decomp, recrystallized from ethyl acetate) NMR(CDCl₃ + DMSO-d₆, δ): 2.69 (s, 3H, CSSCH₃) |

EXAMPLE 17

2.02 g of (1RS)-1-hydroxymethyl-1,2,3,4-tetrahydro-β-carboline are dissolved in 10 ml of dimethylsulfoxide. 1.54 ml of triethylamine and 0.66 ml of carbon disulfide are added thereto. The mixture is stirred at room temperature for 30 minutes. Then, 0.66 ml of methyl iodide is added dropwise thereto. The mixture is stirred at the same temperature for 3 hours. After stirring, the mixture is evaporated to remove the solvent. The residue is dissolved in ethyl acetate, and the solution is washed with water, 5% hydrochloric acid and water successively, dried and evaporated to remove the solvent. The residue is recrystallized from aqueous ethanol, whereby 1.8 g of methyl (1RS)-1-hydroxymethyl-1,2,3,4-tetrahydro-β-carboline-2-carbodithioate are obtained as pale yellow powder. Yield: 62%

NMR (CDCl₃, δ): 2.68 (s, 3H, —CSSCH₃).
Mass (m/e): 292 (M⁺), 244 (M⁺—CH₃S̄H).

EXAMPLES 18 AND 19

In the same manner as described in Example 17, the following compounds are obtained.

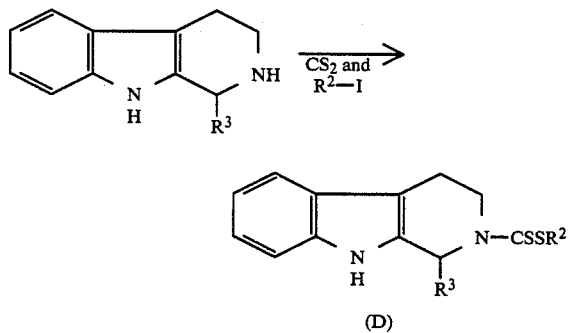

TABLE 7

| Example Nos. | Compounds (D)* R³ | R² | Physical properties and others |
|---|---|---|---|
| 18 | CH₂OH | C₂H₅ | Pale yellow powder NMR (CDCl₃, δ): 1.35 (t, J = 7.5 Hz, 3H, —CSSCH₂CH₃) Mass (m/e): 306 (M⁺), 244 (M⁺—R²SH) Yield: 78% |
| 19 | (CH₂)₃OH | CH₃ | White powder NMR (CDCl₃, δ): 2.63 (s, 3H, —CSSCH₃) Mass (m/e): 320 (M⁺), 272 (M⁺—R²SH) Yield: 95% |

*The compounds listed in the Table 7 are both racemic (i.e. 1RS) modification.

EXAMPLE 20

146 mg of (4RS)-4-hydroxymethyl-1,2,3,4-tetrahydro-β-carboline oxalate, 0.06 ml of carbon disulfide, 0.06 ml of methyl iodide, 0.14 ml of triethylamine and 2 ml of dimethylsulfoxide are treated in the same manner as described in Example 17. 85 mg of methyl (4RS)-4-hydroxymethyl-1,2,3,4-tetrahydro-β-carboline-2-carbodithioate are obtained as pale yellow powder. Yield: 58%

NMR (CDCl₃, δ): 2.69 (s, 3H, —CSSCH₃).
Mass (m/e): 292 (M⁺), 274 (M⁺—H₂O).

EXAMPLE 21

0.88 g of methyl (3S)-3-hydroxymethyl-1,2,3,4-tetrahydro-β-carboline-2-carbodithioate is dissolved in 10 ml of pyridine. 0.43 ml of acetic anhydride is added to the solution, and the mixture is stirred at room temperature for 13 hours. After the reaction, the mixture is poured into 10% hydrochloric acid and then extracted with ethyl acetate. The extract is washed with water, dried and then evaporated to remove the solvent, whereby 0.95 g of methyl (3S)-3-acetoxymethyl-1,2,3,4-tetrahydro-β-carboline-2-carbodithioate is obtained as white powder. Yield: 95%

[α]$_D^{20}$ +118.6° (C=1.0, dioxane).
NMR (CDCl₃, δ): 1.99 (s, 3H, —OCOCH₃).
Mass (m/e): 334 (M⁺).
IRν$_{max}^{nujol}$ (cm⁻¹): 3360, 1735, 1620.

EXAMPLE 22

1.46 g of methyl (3S)-3-hydroxymethyl-1,2,3,4-tetrahydro-β-carboline-2-carbodithioate are dissolved in 50 ml of ether. 10 g of silica gel are added to the solution, and an etheric solution of diazomethane (prepared from 20 g of N-methyl-N-nitrosourea and 60 ml of 40% aqueous solution of potassium hydroxide) is added dropwise thereto. The mixture is stirred at 5° C. for 10 minutes, and again the same amount of silica gel and an etheric solution of diazomethane are added to the mixture. The mixture is further stirred at 5° C. for 2 hours. Silica gel is removed by filtration, and the filtrate is concentrated. The residue is purified by silica gel column chromatography (solvent; n-hexane:ethyl acetate=7:3), whereby 315 mg of methyl (3S)-3-methoxymethyl-1,2,3,4-tetrahydro-β-carboline-2-carbodithioate are obtained as white powder. Yield: 21%

[α]$_D^{20}$30 114.4° (C=1.0, CHCl₃).
NMR (CDCl₃, δ): 2.72 (s, 3H, —CSSCH₃), 3.30 (s, 3H, —OCH₃).
Mass (m/e): 306 (M⁺).

EXAMPLE 23

5.85 g of methyl (3S)-3-hydroxymethyl-1,2,3,4-tetrahydro-β-carboline-2-carbodithioate are dissolved in 40 ml of acetonitrile. 2 ml of dihydropyran and 30 mg of 4-toluenesulfonic acid are added thereto, and the mixture is stirred at room temperature for 2 hours. Further, 4 ml of dihydropyran are added thereto, and the mixture is stirred at the same temperature overnight. After the reaction, the mixture is evaporated to remove the solvent. The residue is dissolved in ethyl acetate, washed with 5% aqueous sodium bicarbonate solution and water successively, dried and evaporated to remove the solvent. The residue is purified by silica gel column chromatography (solvent; n-hexane:ethyl acetate=9:1), whereby 2.63 g of methyl (3S)-3-[(tetrahydropyran-2-yl)oxymethyl]-1,2,3,4-tetrahydro-β-carboline-2-carbodithioate are obtained.

M.p. 151°–154° C. (colorless needles, recrystallized from n-hexane-ethyl acetate).

NMR (CDCl₃, δ): 2.72 (s, 3H, —CSSC$\underline{H}_3$), 7.88 (s, 1H, —N$\underline{H}$).
Mass (m/e): 376 (M⁺).
IR$\nu_{max}^{nujol}$ (cm⁻¹): 3460 (N—H).

PREPARATION OF STARTING COMPOUNDS

Preparation 1

(1) 0.93 g of 5-fluoro-L-tryptophan methyl ester hydrochloride is dissolved in 14 ml of methanol. 0.52 g of 35% formalin is added thereto and the mixture is stirred at room temperature for 20 hours. Ether is added to the mixture and crystalline precipitates are collected by filtration, washed with ether and dried, whereby 0.66 g of methyl (3S)-6-fluoro-1,2,3,4-tetrahydro-β-carboline-3-carboxylate hydrochloride are obtained as colorless needles. Yield: 68%
M.p. 246°–248° C.
NMR (DMSO-d₆, δ): 3.80 (s, 3H, —COOC$\underline{H}_3$).
IR$\nu_{max}^{nujol}$ (cm⁻¹): 1745.

(2) A mixture of 0.577 g of methyl (3S)-6-fluoro-1,2,3,4-tetrahydro-β-carboline-3-carboxylate hydrochloride, 0.32 g of sodium borohydride, 20 ml of ethanol and 10 ml of water is stirred at room temperature for 21 hours, and then further refluxed for 3 hours. After the reaction, insoluble materials are removed by filtration and washed with hot ethanol. The filtrate and washings are combined and concentrated. Water is added to the residue, and crystalline precipitates are collected by filtration and dried, whereby 286 mg of (3S)-3-hydroxymethyl-6-fluoro-1,2,3,4-tetrahydro-β-carboline are obtained as colorless needles. Yield: 65%
M.p. 210°–211° C. (decomp.).
Mass (m/e): 220 (M⁺).

Preparations 2 to 6

(1) In the same manner as described in Preparation 1-(1), the following compounds are obtained.

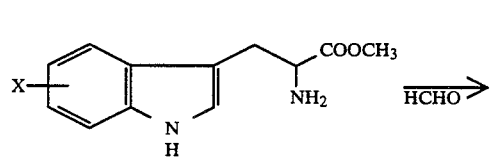

(E)

TABLE 8

| Preparation Nos. | Compounds (E)* X (Salts) | Yield (%) | Physical properties |
|---|---|---|---|
| 2-(1) | 6-Cl (hydrochloride) | 56 | M.p. 248 to 250° C. (decomp.) Colorless prisms NMR (DMSO-d₆, δ): 3.81 (s, 3H, —COOC$\underline{H}_3$) IR $\nu_{max}^{nujol}$ (cm⁻¹): 1755 |
| 3-(1) | 6-Br (hydrochloride) | 56 | M.p. 254 to 256° C. (decomp.) Colorless needles NMR (DMSO-d₆, δ): 3.82 (s, 3H, —COOC$\underline{H}_3$) IR $\nu_{max}^{nujol}$ (cm⁻¹): 1750 |
| 4-(1) | 6-CH₃ (hydrochloride) | 80 | M.p 284 to 285° C. (decomp.) Colorless needles NMR (CDCl₃ + DMSO-d₆, δ): 2.41 (s, 3H, C$\underline{H}_3$—⌬—) 3.88 (s, 3H, —COOC$\underline{H}_3$) IR $\nu_{max}^{nujol}$ (cm⁻¹): 1760 |
| 5-(1) | 8-CH₃ (free base) | 63 | M.p 146 to 148° C. Pale yellow prisms NMR (CDCl₃ + DMSO-d₆, δ): 2.46 (s, 3H, ⌬—CH₃) 3.77 (s, 3H, —COOC$\underline{H}_3$) IR $\nu_{max}^{nujol}$ (cm⁻¹): 1710 |
| 6-(1) | 6-O—CH₂—⌬ (hydrochloride) | 77 | M.p 248 to 250° C. (decomp.) Pale yellow needles NMR (CDCl₃ + DMSO-d₆, δ): 3.85 (s, 3H, —COOC$\underline{H}_3$) 5.05 (s, 2H, —OC$\underline{H}_2$—⌬) IR $\nu_{max}^{nujol}$ (cm⁻¹): 1760 |

*The compounds listed in the Table are all (3S)—isomers.

(2) In the same manner as described in Preparation 1-(2), the following compounds are obtained.

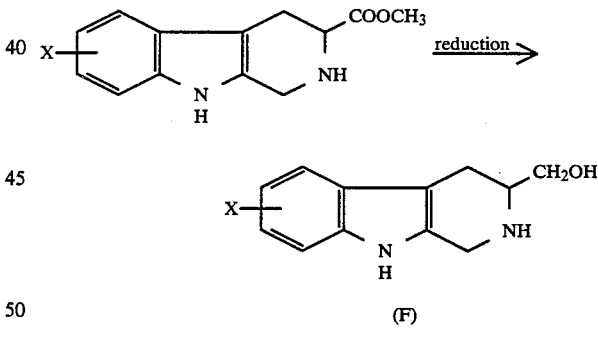

(F)

TABLE 9

| Preparation Nos. | Compounds (F)* —X | Yield (%) | Physical properties |
|---|---|---|---|
| 2-(2) | 6-Cl | 52 | M.p 225 to 227° C. (decomp.) Colorless prisms Mass (m/e): 236 (M⁺) |
| 3-(2) | 6-Br | 89 | M.p. 236 to 238° C. Colorless needles Mass (m/e): 280, 282 (M⁺) |
| 4-(2) | 6-CH₃ | 73 | M.p. 206 to 207° C. Colorless prisms Mass (m/e): 216 (M⁺) |
| 5-(2) | 8-CH₃ | 63 | M.p. 246 to 248° C. Colorless needles Mass (m/e): 216 (M⁺) |

TABLE 9-continued

| Preparation Nos. | Compounds (F)* −X | Yield (%) | Physical properties |
|---|---|---|---|
| 6-(2) | 6-O—CH₂—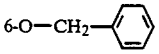 | 67 | M.p. 152 to 153° C. Pale yellow needles Mass (m/e): 308 (M+) |

*The compounds listed in the Table are all (3S—)isomers.

Preparation 7

198 mg of (3S)-3-hydroxymethy-6-benzyloxy-1,2,3,4-tetrahydro-β-carboline are dissolved in 10 ml of ethanol. 300 mg of 10% palladium-charcoal are added thereto, and the mixture is subjected to catalytic reduction in hydrogen gas under atmospheric pressure. After the reaction, the mixture is filtered, and the filtrate is concentrated. The residue is triturated with ether, whereby 73 mg of (3S)-3-hydroxymethyl-6-hydroxy-1,2,3,4-tetrahydro-β-carboline are obtained as pale yellow powder. Yield: 53%

Mass (m/e): 218 (M+).

Preparation 8

A mixture of 111 mg of 5-fluoro-L-tryptophan, 50 mg of 35% formalin, 0.8 ml of 0.1N sulfuric acid, 0.4 ml of ethanol and 0.3 ml of water is stirred at room temperature for 24 hours. The precipitates are collected by filtration, washed with water and ethanol and then dried. 80 mg of (3S)-6-fluoro-1,2,3,4-tetrahydro-β-carboline-3-carboxylic acid are obtained as white powder. Yield: 69%

Mass (m/e): 234 (M+).

Preparation 9 to 13

In the same manner as described in Preparation 8, the following compounds are obtained.

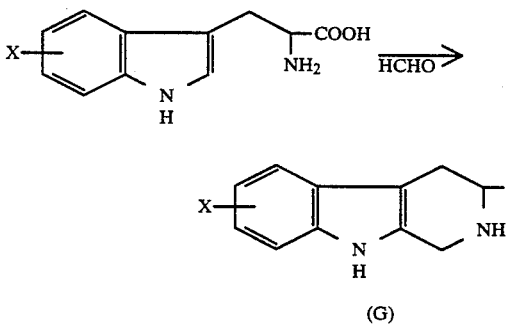

(G)

TABLE 10

| Preparation Nos. | Compound (G) X | Configuration | Yield (%) | Mass (m/e) (M+) |
|---|---|---|---|---|
| 9 | 6-Cl | 3R | 99 | 250 |
| 10 | 6-CH₃ | 3S | 86 | 230 |
| 11 | 6-OH | 3RS | 91 | 232 |
| 12 | 6-OCH₃ | 3S | 81 | 246 |
| 13 | 6-OCH₂—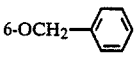 | 3S | 97 | 322 |

Preparation 14

3.02 g of 7-methyl-L-tryptophan methyl ester are dissolved in 20 ml of methanol, and 4 ml of 15% HCl-methanol are added thereto. The mixture is evaporated to remove the solvent. The residue is dissolved in 30 ml of methanol, and 2.86 g of 35% formalin are added thereto. The mixture is stirred at room temperature overnight. The mixture is evaporated to remove the solvent, and water is added to the residue. The aqueous solution is adjusted to pH 10 with 10% aqueous ammonia, and extracted with ethyl acetate. The extract is washed with water, dried and then evaporated to remove the solvent. The residue is recrystallized from chloroform. 2.0 g of methyl (3S)-8-methyl-1,2,3,4-tetrahydro-β-carboline-3-carboxylate are obtained as pale yellow prisms. Yield: 63%

M.p. 146°–148° C.

Mass (m/e): 244 (M+).

IR$\nu_{max}^{nujol}$ (cm$^{-1}$): 1710.

Preparation 15

(a) 5.09 g of L-tryptophan methyl ester hydrochloride are dissolved in 60 ml of methanol. 1.89 g of 35% formalin are added thereto, and the mixture is stirred at room temperature overnight. After distilling off the solvent, the resulting residue is recrystallized from methanol. 4.42 g of methyl (3S)-1,2,3,4-tetrahydro-β-carboline-3-carboxylate hydrochloride are obtained as colorless needles. Yield: 82.9%

M.p. 250°–253° C.

The hydrochloride obtained above is dissolved in water and is treated with aqueous ammonia to give the corresponding free base.

M.p. 168°–170° C.

$[\alpha]_D^{20}$ −64.3° (C=1.1, methanol).

(b) A mixture of 15 g of methyl (3S)-1,2,3,4-tetrahydro-β-carboline-3-carboxylate, 6.99 g of NaBH₄, and 225 ml of 80% ethanol is stirred at room temperaure for 12 hours, and then refluxed for 1.5 hours. The insoluble materials are filtered off and washed with hot ethanol. The filtrate and the washing are combined and distilled to remove the solvent. Water (40 ml) is added to the residue, and the solution is stirred for 40 minutes. The precipitates are collected by filtration, dried and then recrystallized from ethanol. 9.03 g of (3S)-3-hydroxymethyl-1,2,3,4-tetrahydro-β-carboline are obtained as colorless needles. Yield: 79.4%

M.p. 191°–193° C.

$[\alpha]_D^{20}$ −84.6° (c=1.0, methanol).

(c) 2.02 g of (3S)-3-hydroxymethyl-1,2,3,4-tetrahydro-β-carboline are dissolved in 24 ml of methanol, and 1.5 ml of triethylamine and 1.8 ml of benzyloxycarbonyl chloride are added dropwise to the mixture. The mixture is stirred at 5°–10° C. for 3 hours, and the mixture is evaporated to remove the solvent. The residue is dissolved in ethyl acetate. The solution is washed with water, a 0.5M citric acid solution and water, dried and then evaporated to remove the solvent. 2.90 g of (3S)-2-benzyloxycarbonyl-3-hydroxymethyl-1,2,3,4-tetrahydro-β-carboline are obtained as colorless oil. Yield: 86%

Mass (m/e): 366 (M+).

(d) 11.24 g of (3S)-2-benzyloxycarbonyl-3-hydroxymethyl-1,2,3,4-tetrahydro-β-carboline are dissolved in 40 ml of pyridine. 7.01 g of p-toluenesulfonyl chloride are added dropwise to the mixture of 5° C., and the mixture is stirred at the same temperature for 30 minutes. The mixture is evaporated under reduced pressure to remove the solvent. The residue is dissolved in ethyl acetate, and the solution is washed with 5% HCl and water, dried and then evaporated to remove the solvent.

The residue is dissolved in 50 ml of dimethylformamide, and the solution is added dropwise to a suspension of 2.21 g of sodium cyanide in 40 ml of dimethylformamide. The addition is carried out at 5° C. The mixture is stirred at the same temperature for 2 hours, and then at room temperature for 60 hours. The mixture is evaporated under reduced pressure to remove the solvent. Water is added to the residue, and the aqueous solution is extracted with ethyl acetate. The extract is washed with water, dried and then evaporated to remove the solvent. The residue is purified by silica gel column chromatography (Solvent; ethyl acetate:n-hexane=1:2). 3.78 g of (3S)-2-benzyloxycarbonyl-3-cyanomethyl-1,2,3,4-tetrahydro-β-carboline are obtained as pale red oil. Yield: 36%

Mass (m/e): 345 (M+).

(e) 1.89 g of (3S)-2-benzyloxycarbonyl-3-cyanomethyl-1,2,3,4-tetrahydro-β-carboline are dissolved in 30 ml of methanol. The solution is saturated with gaseous hydrogen chloride as 5° C., and the saturated solution is allowed to stand at the same temperature for one hour. The solution is evaporated under reduced pressure to remove the solvent. The residue is dissolved in ethyl acetate, and the solution is washed with water, dried and then evaporated to remove the solvent. The residue is purified by silica gel column chromatography (Solvent; ethyl acetate:n-hexane=1:2). 0.90 g of methy (3S)-2-benzyloxycarbonyl-1,2,3,4-tetrahydro-β-carboline-3-acetate is obtained as colorless needles. Yield: 43%

M.p. 174°-176° C.

(f) 0.87 g of methyl (3S)-2-benzyloxycarbonyl-1,2,3,4-tetrahydro-β-carboline-3-acetate is dissolved in 12 ml of tetrahydrofuran, and 5 ml of 1N NaOH are added thereto. The mixture is stirred at room temperature for 16 hours. The mixture is evaporated to remove the solvent. The residue is dissolved in water, and the aqueous solution is extracted with ethyl acetate. The aqueous layer is acidified with 10% HCl, and extracted with ethyl acetate. The extract is washed with a saturated aqueous sodium chloride solution, dried and then evaporated to remove the solvent. 630 mg of (3S)-2-benzyloxycarbonyl-1,2,3,4-tetrahydro-β-carboline-3-acetic acid are obtained as pale yellow powder. Yield: 75%

Mass (m/e): 364 (M+).

(g) 0.55 g of (3S)-2-benzyloxycarbonyl-1,2,3,4-tetrahydro-β-carboline-3-acetic acid is dissolved in 12 ml of 80% aqueous ethanol. 0.5 g of 10% Pd-C and 3 ml of 10% HCl are added to the solution. The mixture is subjected to catalytic reduction in hydrogen gas under atmospheric pressure at room temperature. The catalyst is filtered off, and washed with ethanol. The filtrate and the washings are combined, and evaporated to remove the solvent. The residue is recrystallized from ethyl acetate. 290 mg of (3S)-1,2,3,4-tetrahydro-β-carboline-3-acetic acid hydrochloride are obtained as pale yellow needles. Yield: 72%

M.p. 233°-235° C. (decomp.).

Preparation 16

(1) 2.04 g of methyl 3-amino-2-(indol-3-yl)propionate hydrochloride are dissolved in 60 ml of methanol. 0.83 g of 35% formalin is added thereto, and the mixture is stirred at room temperature for 18 hours. After the reaction, ether is added to the mixture and crystalline precipitates are collected by filtration and dried, whereby 2.04 g of methyl (4RS)-1,2,3,4-tetrahydro-β-carboline-4-carboxylate hydrochloride are obtained as colorless needles. Yield: 95%

M.p. 223°-225° C.

The hydrochloride obtained above is neutralized with 6% potassium carbonate to give the corresponding free base.

M.p. 172°-174° C.

(2) 1.12 g of methyl (4RS)-1,2,3,4-tetrahydro-β-carboline-4-carboxylate are dissolved in 34 ml of tetrahydrofuran. The solution is added dropwise to a suspension of 0.365 g of lithium aluminum hydride in 10 ml of dry tetrahydrofuran at 5° C. The mixture is stirred at room temperature for 2.5 hours. After the reaction, aqueous tetrahydrofuran is added to the mixture, and insoluble materials are removed by filtration. The filtrate is evaporated to remove the solvent. The residue is dissolved in methanol, and 0.73 g of oxalic acid dihydrate are added thereto, and the mixture is allowed to stand at room temperature. Resulting crystals are collected by filtration and dried, whereby 1.17 g of (4RS)-4-hydroxymethyl-1,2,3,4-tetrahydro-β-carboline oxalate are obtained as pale yellow needles. Yield: 83%

M.p. 226°-227° C.

Preparation 17

30.3 g of (3S)-3-hydroxymethyl-1,2,3,4-tetrahydro-β-carboline are dissolved in a mixture of 300 ml of methanol and 80 ml of water. 15.9 g of triethylamine and 11.9 g of carbon disulfide are added thereto. The mixture is stirred at 20° C. for 30 minutes. 22.35 g of methyl iodide are added dropwise thereto. The mixture is stirred at 20° to 25° C. for 1.5 hour. After stirring, the mixture is evaporated to remove the solvent. The residue is dissolved in ethyl acetate, washed with 5% hydrochloric acid and water, dried and evaporated to remove the solvent. The residue is recrystallized from aqueous ethanol, whereby 42.0 g of methyl (3S)-3-hydroxymethyl-1,2,3,4-tetrahydro-β-carboline-2-carbodithioate are obtained as colorless needles. Yield: 90%

M.p. 114°-116° C.

$[\alpha]_D^{20}$ +159.0° (C=1.0, methanol).

NMR(CDCl$_3$, δ): 2.62 (s, 3H, —CSSCH$_3$).

Mass (m/e): 292 (M+), 244 (M+—CH$_3$SH).

What we claim is:

1. A tetrahydro-β-carboline derivative of the formula:

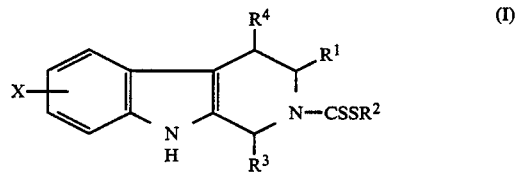

wherein R$^2$ is lower alkyl, and either (A)

R$^1$ is hydroxymethyl or carboxy,

R$^3$ and R$^4$ are both hydrogen, and

X is halogen, lower alkyl, lower alkoxy, hydroxy or benzyloxy; or (B)

R$^1$ is hydrogen, carboxy-lower alkyl or a group of the formula: —CH$_2$OY,

Y is lower alkyl, lower alkanoyl or an oxygen-containing monocyclic heterocyclic group selected from the group consisting of tetrahydropyranyl, dihydropyranyl and tetrahydrofuryl, R$^3$ is hydrogen, hydroxy-lower alkyl or carboxy, R$^4$ is hydrogen or hydroxy-lower alkyl, and X is hydrogen
or a pharmaceutically acceptable salt thereof.

2. The compound claimed in claim 1, wherein $R^2$ is methyl or ethyl, and either (A)
- $R^1$ is hydroxymethyl or carboxy,
- $R^3$ and $R^4$ are both hydrogen, and
- X is fluorine, chlorine, bromine, methyl, methoxy, hydroxy or benzyloxy; or (B)
- $R^1$ is hydrogen, carboxymethyl or a group of the formula: —CH$_2$OY,
- Y is methyl, acetyl or tetrahydropyranyl,
- $R^3$ is hydrogen, hydroxymethyl, hydroxypropyl or carboxy,
- $R^4$ is hydrogen or hydroxymethyl, and
- X is hydrogen.

3. The compound claimed in claim 1, wherein $R^1$ is hydroxymethyl or carboxy, $R^2$ is lower alkyl, $R^3$ and $R^4$ are both hydrogen, and X is halogen, lower alkyl, lower alkoxy, hydroxy or benzyloxy.

4. The compound claimed in claim 1, wherein $R^1$ is hydrogen, carboxy-lower alkyl or a group of the formula: —CH$_2$OY, Y is lower alkyl, lower alkanoyl or an oxygen containing monocyclic heterocyclic group selected from the group consisting of tetrahydropyranyl, dihydropyranyl and tetrahydrofuryl, $R^2$ is lower alkyl, $R^3$ is hydrogen, hydroxy-lower alkyl or carboxy, $R^4$ is hydrogen or hydroxy-lower alkyl, and X is hydrogen.

5. The salt of the compound claimed in claim 3, wherein $R^1$ is carboxy.

6. The salt of the compound claimed in claim 4, wherein $R^1$ is carboxy-lower alkyl or $R^3$ is carboxy.

* * * * *